United States Patent [19]

Clark

[11] Patent Number: 4,611,382

[45] Date of Patent: Sep. 16, 1986

[54] METHOD FOR MANUFACTURING A FISTULA

[75] Inventor: Julie L. Clark, Livingston, N.J.

[73] Assignee: Joule' Inc., Orange, N.J.

[21] Appl. No.: 602,685

[22] Filed: Apr. 23, 1984

[51] Int. Cl.⁴ ............... B23P 11/02; B29C 47/00; A61M 5/32

[52] U.S. Cl. .................... 29/450; 29/557; 29/DIG. 37; 264/145; 264/148; 264/150; 264/153; 604/177; 604/192; 604/240

[58] Field of Search ........... 29/450, 557, DIG. 37; 604/177, 187, 192, 263, 283, 240, 241; 264/145, 148, 150, 153

[56] References Cited

U.S. PATENT DOCUMENTS

| | | | |
|---|---|---|---|
| 2,539,510 | 1/1951 | Friden | 604/192 |
| 3,179,727 | 4/1965 | Taylor | 264/148 |
| 3,756,235 | 9/1973 | Burke et al. | 604/240 |
| 3,825,002 | 7/1974 | Paige | 604/241 |
| 4,192,304 | 3/1980 | Millet | 604/177 |
| 4,413,992 | 11/1983 | Soika | 604/283 |
| 4,447,479 | 5/1984 | Harrison | 264/148 |

OTHER PUBLICATIONS

Nayler, J. L. and Nayler, G. H. F.; Dictionary of Mechanical Engineering; George Newnes, Ltd., London (1967); at 32 (definition of "blanking").

Primary Examiner—Howard N. Goldberg
Assistant Examiner—R. S. Wallace
Attorney, Agent, or Firm—Stoll, Wilkie, Previto and Hoffman

[57] ABSTRACT

A method of manufacturing a fistula consisting of a needle mounted on a plastic handle or wing. The plastic wings are formed by continuously extruding a plastic strip having the wing cross section. The outer end of the extruded plastic is blanked to partially shape and outline an individual wing. Thereafter, a needle is inserted into a hollow core on the endmost partially blanked wing and a needle guard is positioned over the needle. Finally, the completed fistula is removed from the end of the extruded strip by a final cut or punching for producing a finished fistula.

4 Claims, 4 Drawing Figures

U.S. Patent  Sep. 16, 1986  4,611,382
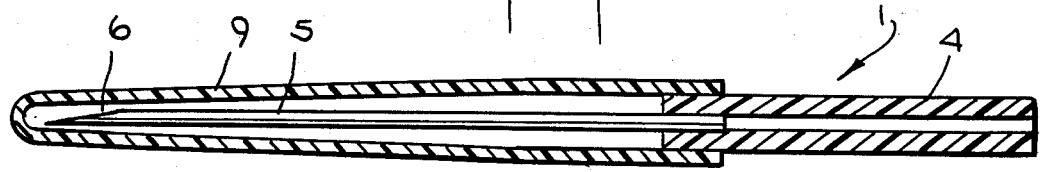
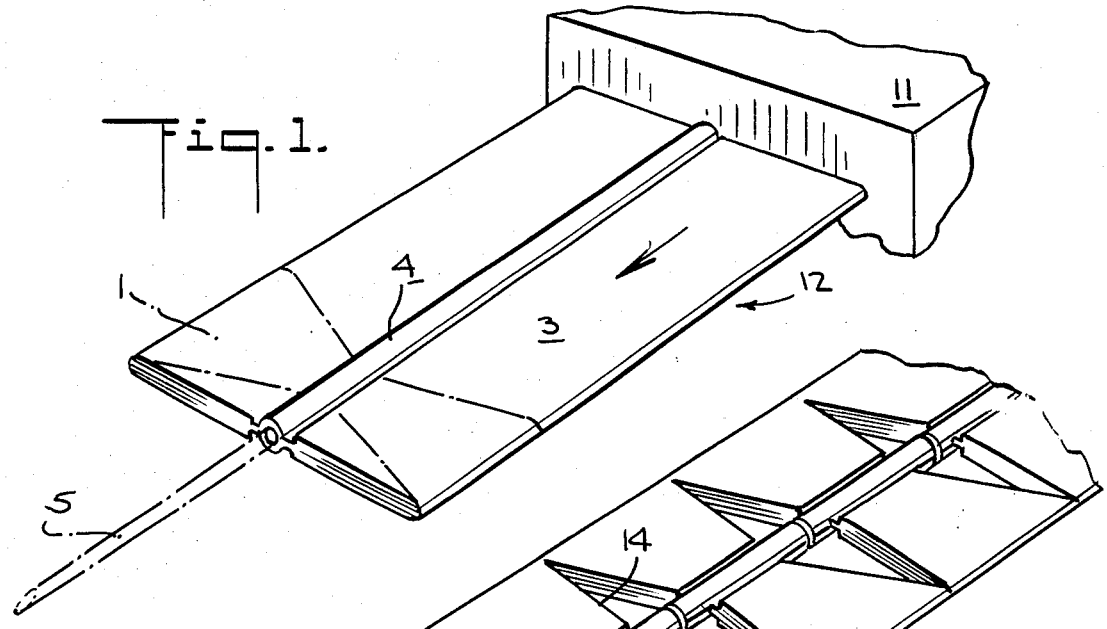
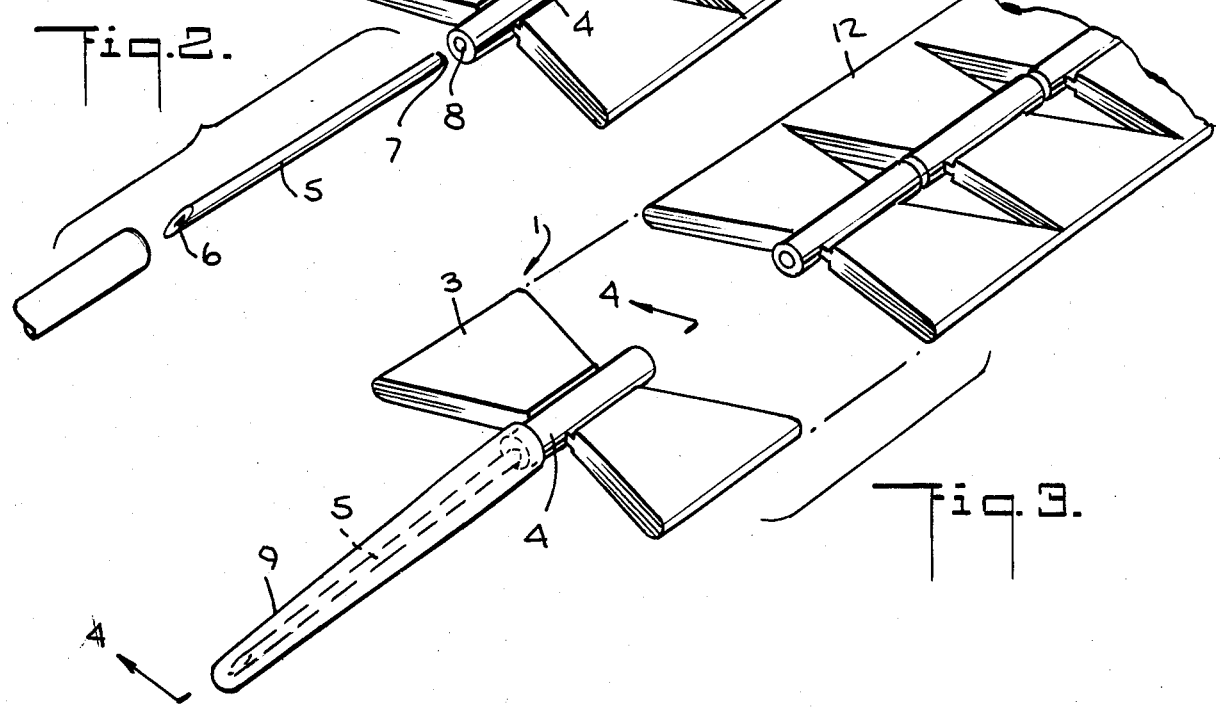

METHOD FOR MANUFACTURING A FISTULA

BACKGROUND OF THE INVENTION

The present invention is directed to fistulas or scalp vein sets and more particularly to an improved, more efficient, and less expensive method of manufacturing fistulas. Fistulas are used in enormous quantities in clinics and hospitals for penetrating patient's bodies in a number of differing applications. For example, fistulas are used in fluid delivery systems in intravenous feeding and the like. Additionally, fistulas are used for handling blood such as recirculating a patient's blood during kidney dialysis.

Typical fistulas comprise a steel or stainless steel needle for insertion into the patient's body using a plastic handle or wing attached to the outer end of the needle. The manufacture of fistulas or scalp vein sets requires the steps of shaping the plastic handles and of fastening the needles into the handles with a safety guard applied over the needle.

The present manufacturing practice includes the steps of individually forming the plastic handles or wings by injection molding and thereafter inserting the needles into the individual wings. The wings, for example, are now injection molded and a needle is inserted as a molded insert. It is the general object of the present invention to provide a new and more efficient method of manufacturing the fistulas whereby their cost may be significantly reduced.

It is a further object of the present invention to provide a new fistula and method for its manufacture wherein the plastic wing is formed by an extrusion and blanking operation and where the completed fistula is formed by related operations in this extrusion and blanking operation.

Other and further objects of the present invention will become apparent upon an understanding of the illustrative embodiments about to be described, or will be indicated in the appended claims, and various advantages not referred to herein will occur to one skilled in the art upon employment of the invention in practice.

BRIEF DESCRIPTION OF THE DRAWINGS

A preferred embodiment of the invention has been chosen for purposes of illustration and description and is shown in the accompanying drawings, forming a part of the specification, wherein:

FIG. 1 is a perspective view illustrating the extrusion of a fistula blank in accordance with the present invention.

FIGS. 2 and 3 are perspective views of the extruded fistula blanks and related fistula components illustrating the fistula blanking and assembly steps.

FIG. 4 is a sectional view of a completed fistula taken along line 4—4 on FIG. 3.

DESCRIPTION OF THE PREFERRED EMBODIMENT

FIG. 1 illustrates a finished fistula 1 manufactured in accordance with the method of this invention. The fistula 1 includes a plastic wing 3 with a hollow core 4 mounting a needle 5 having a bevelled tip 6 and an opposite blunt end 7 inserted into the hollow center 8 of the plastic wing 3 core 4. The plastic wing 3 is formed of a relatively soft plastic permitting the clinician to tightly grip the wing 3 and to fold it in a convenient manner. The blunt end 7 of the needle 5 is flush with the top portion of a wing core 4. A molded plastic guard 9 is slipped over the needle 5 with its inner end frictionally engaging the projecting end 10 of the wing core 4.

FIG. 1 is a diagramatic illustration of the method of manufacturing the above described fistula 1. A conventional plastic extruding machine is illustrated at 11. A suitable die is shaped to extrude the plastic as a strip 12 having a cross section corresponding to that of the wing 3 (FIG. 2). This extruded strip 12 of plastic of indeterminate length thus has a cross section generally as illustrated in sectional FIG. 2.

A second step in the formation of the wing 3 is performed by a blanking operation at a blanking station 13 where generally triangular blanked cut-outs 14 partially define the wing 3 and form the opposite ends of the hollow wing core 4. At the station 13 the needle 5 is inserted into the core 4 with its blunt end 7 on a level with the inner end of the wing core 4. Epoxy is used to fasten the needle 5 in position and then a hollow guard 9 is slipped over the mounted needle 5.

In a final step at a second punch or blanking position 15, the wing 3 is cut completely clear of the end of the extruded strip 12. In the preferred method described above, the assembly of the fistula 1, while it remains partially attached to the extruded strip, facilitates the handling of the wing portions 3 to simplify the assembly of the fistula. Alternatively, the needle 5 and guard 9 may be mounted on the wing 3 after it has been completely cut or blanked from the extruded strip 12.

By either method an inexpensive and rapid means is provided to form the wing 3 and to assemble the wing 3 with the needle 5 and the guard 9 in a completed fistula 1. The method eliminates a number of intermediate steps presently required in the manufacturing systems employing separate injection molded wing portions.

It will be seen that an improved fistula and method of manufacture has been disclosed which results in a significant saving in manufacturing time and therefore in the cost of the fistula or scalp vein sets. This will provide a significant cost saving for this product in its important medical uses.

As various changes may be made in the form, construction and arrangement of the invention and without departing from the spirit and scope of the invention, and without sacrificing any of its advantages, it is to be understood that all matter herein is to be interpreted as illustrative and not in a limiting sense.

Having thus described my invention, I claim:

1. A method of manufacturing a fistula comprising the steps of:
   extruding a plastic strip of indeterminate length having a pre-determined cross section with spaced flaring wing-like portions extending outwardly from a hollow core portion;
   blanking the endmost portion of said strip for defining individual flared wing-like members in said wing-like portions extending outwardly from said core portion;
   inserting a hollow core needle into said plastic core portion with the inserted end of said needle being positioned at a rearwardmost portion of the blanked wing-like member;
   placing a hollow molded guard member over said needle with said guard frictionally engaging an end portion of said core portion;

cutting said blanked endmost portion free from the remainder of said extruded plastic strip thereby forming a completed fistula with taper wing portions and a succeeding forward wing portion.

2. The method as claimed in claim 1 in which said first blanking step comprises forming generally triangular cutouts in said extruded plastic strip.

3. The method as claimed in claim 1 which further comprises molding said wing-like portions with relatively thin cross-sections extending outwardly from a generally cylindrical hollow core portion.

4. The method as claimed in claim 1 in which said blanking forms an endmost portion on said core portion extending beyond said wing-like members and having a generally cylindrical outer surface engaging said guard.

* * * * *